United States Patent
Nubel et al.

(10) Patent No.: US 7,135,596 B2
(45) Date of Patent: Nov. 14, 2006

(54) METHOD OF REMOVING IRON CONTAMINANTS FROM LIQUID STREAMS DURING THE MANUFACTURE AND/OR PURIFICATION OF AROMATIC ACIDS

(75) Inventors: Philip O. Nubel, Naperville, IL (US); Timothy H. Keyes, Charleston, SC (US); Ricky L. Wittman, Aurora, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 10/420,092

(22) Filed: Apr. 22, 2003

(65) Prior Publication Data
US 2004/0044246 A1    Mar. 4, 2004

Related U.S. Application Data

(60) Provisional application No. 60/374,719, filed on Apr. 23, 2002.

(51) Int. Cl.
*C07C 51/255* (2006.01)
*C07C 51/42* (2006.01)
(52) U.S. Cl. .................. 562/414; 562/412; 562/485
(58) Field of Classification Search .................. 134/3; 562/410, 412, 409, 485, 487, 416, 414
See application file for complete search history.

(56) References Cited

U.S. PATENT DOCUMENTS

| | | | |
|---|---|---|---|
| 3,393,975 A | 7/1968 | Mitchell et al. | 23/123 |
| 4,394,299 A | 7/1983 | Puskas et al. | 252/447 |
| 4,629,715 A | 12/1986 | Schroeder | 502/185 |
| 4,728,630 A | 3/1988 | Schroeder et al. | 502/185 |
| 4,892,972 A | 1/1990 | Schroeder et al. | 562/487 |
| 5,354,898 A | 10/1994 | Schroeder | 562/485 |
| 5,362,908 A | 11/1994 | Schroeder et al. | 562/487 |
| 5,612,007 A | 3/1997 | Abrams | 422/189 |
| 5,723,656 A * | 3/1998 | Abrams | 562/412 |
| 5,929,274 A * | 7/1999 | Lamshing et al. | 562/487 |
| 6,504,051 B1 | 1/2003 | Miller, Jr. et al. | 562/409 |
| 2003/0098042 A1* | 5/2003 | Belmonte et al. | 134/3 |

FOREIGN PATENT DOCUMENTS

WO    WO 0153246    7/2001

OTHER PUBLICATIONS

Grant et al, chemical dictionary, 5 th ed., 1987, p. 292.*
Centerline, vol. 5, No. 2, Summer 2001, pp. 6-8, 15-18, published by Mary Kay O'Connor Process Safety Center).

* cited by examiner

*Primary Examiner*—Taylor Victor Oh
(74) *Attorney, Agent, or Firm*—Stephen L. Hensley

(57) ABSTRACT

This invention relates to control or removal of amounts of dissolved iron that may be present in liquid process streams in the manufacture of aromatic acids. The present invention further relates to the control or removal of dissolved iron contaminants present in liquid streams during the manufacture of a crude aromatic acid. The present invention also further relates to the control or removal of dissolved iron contaminants present in liquid streams during the purification of a crude aromatic acid. The present invention also further relates to controlling of decreasing the formation of iron oxides on the surfaces of equipment used during the manufacture of crude aromatic acid and/or purification of crude aromatic acid.

30 Claims, 1 Drawing Sheet

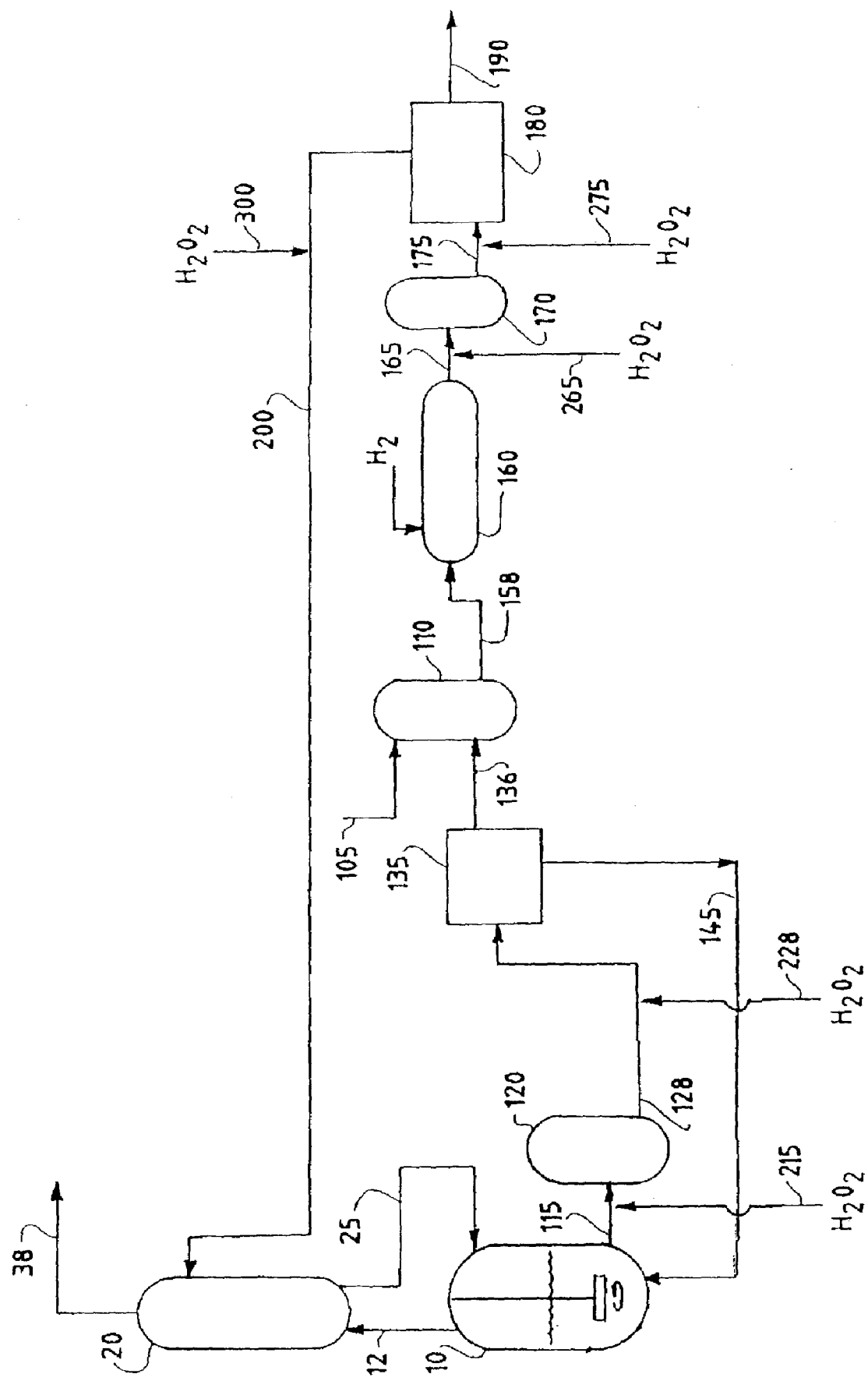

US 7,135,596 B2

METHOD OF REMOVING IRON CONTAMINANTS FROM LIQUID STREAMS DURING THE MANUFACTURE AND/OR PURIFICATION OF AROMATIC ACIDS

This application claims the benefit of U.S. of America provisional Patent Application No. 60/374,719, filed Apr. 23, 2002, which is incorporated herein by reference.

FIELD OF THE INVENTION

This invention relates to control or removal of dissolved iron that is or may be present in liquid process streams in the manufacture of aromatic carboxylic acids. The present invention further relates to the control or removal of dissolved iron contaminants present in liquid streams during the manufacture of a crude aromatic acid. The present invention also further relates to the control or removal of dissolved iron contaminants present in liquid streams during the purification of a crude aromatic acid. The present invention also further relates to decreasing the formation of iron oxides on the surfaces of equipment used during the manufacture of crude aromatic acid and/or purification of crude aromatic acid.

BACKGROUND OF THE INVENTION

Aromatic acids comprise at least one aromatic ring, typically a benzene or naphthalene ring, substituted by at least one carboxylic acid group. Examples of aromatic acids include phthalic acid, isophthalic acid, terephthalic acid, 2,6 naphthalene dicarboxylic acid, and benzoic acid. When reacted with other monomers such as diols (e.g. ethylene glycol), aromatic acids may be used to make useful polymers such as polyesters (e.g. polyethylene terephthalate). These resulting polyesters are useful in a variety of applications including containers, films, packaging materials, fibers, and others.

Aromatic acids are typically manufactured by an aromatic oxidation process wherein a feedstock comprising an aromatic compound substituted with at least one oxidizable group such as alkyl or acyl group or combinations thereof is oxidized to form a crude aromatic acid. Typical feedstocks suitable for oxidation to form aromatic acids include orthoxylene, meta-xylene, paraxylene, 1,5 dimethylnaphthalene, 2,6 dimethylnaphthalene, and the like. The feedstock is typically oxidized in a reactor in the presence of a carboxylic acid solvent, oxidation catalyst, and a source of oxygen. The catalyst used in the oxidation process typically comprises one or more oxidation catalyst metals, including those metals having an atomic number of about 21 to about 82.

The aromatic oxidation process is typically an exothermic oxidation reaction, which results in the formation of a crude aromatic acid product in an oxidation reactor. Typically, the crude aromatic acid precipitates to form an oxidation slurry with a solid phase comprising precipitated crude aromatic acid product and an oxidation liquid stream. The oxidation liquid stream comprises the carboxylic acid solvent, water, and various materials in solution including unreacted feedstock, unprecipitated crude aromatic acid product, unprecipitated oxidation reaction by-products and oxidation catalyst materials, e.g. cobalt, manganese and bromine. The crude aromatic acid product may be separated from the oxidation liquid stream by subjecting the oxidation slurry to a solid-liquid separation step. Once separated from the crude aromatic acid product, the oxidation liquid stream is often also termed as "oxidation mother liquor." All or a portion of this oxidation mother liquor is frequently recycled, i.e. returned, to the oxidation reactor.

The crude aromatic acid product is typically purified in an aromatic acid purification process wherein the crude aromatic acid product is dissolved in water and treated with hydrogen and a hydrogenation catalyst under elevated temperature and pressure. After temperature and pressure are reduced, the aromatic acid purification process yields a purification slurry with a solid phase comprising precipitated purified aromatic acid product and a purification liquid stream. The purified aromatic acid may be separated from the purification liquid stream by subjecting the purification slurry to a solid-liquid separation step. Once separated from the purified aromatic acid product, the purification liquid stream is often referred to as a "purification mother liquor." The purification mother liquor usually is predominantly water and typically comprises minor amounts of additional components such as soluble hydrogenation by-products and, when purification is conducted as part of an integrated aromatic acid manufacturing process comprising oxidation and purification steps, may also contain residual carboxylic acid and minor amounts of oxidation catalyst metals. Purification mother liquor, or a portion thereof remaining after removal of soluble by-products, frequently is recycled in whole or in part to the process.

Certain problems are encountered during the aforementioned aromatic oxidation process and aromatic acid purification process which result from the contamination of liquid streams with dissolved iron. This dissolved iron contamination typically results when liquid streams are directed and exposed to iron-containing surfaces of equipment used during these processes. For example, oxidation and/or purification mother liquor is typically directed and exposed to iron-containing surfaces of equipment. Problems associated with dissolved iron contamination may be ameliorated by decreasing the exposure of liquid streams to iron-containing surfaces of equipment, such as by alternative use of solid titanium or titanium-clad equipment. Nevertheless, because of the relatively high expense of titanium, the exposure of liquid streams to iron-containing surfaces of equipment (e.g. stainless steel) remains a typical occurrence. Examples of equipment having iron-containing surfaces include pumps, transfer lines, vessels, and the like. Dissolved iron contamination is undesirable because of its potential to precipitate as iron oxide. Accumulation of iron oxide over time will typically begin to negatively affect the usefulness of a piece of equipment. For example, accumulation of iron oxide on the surface of titanium cladding may promote accelerated corrosion. Accordingly, it would be desirable to discover a method for removing dissolved iron from oxidation and/or purification liquid streams.

The problems associated with precipitation of iron from liquid streams contaminated with dissolved iron may be better understood with reference to the effects on particular equipment items. The aromatic oxidation process involves an exothermic reaction typically producing an off-gas comprising vaporized solvent and vaporized water. This off-gas or a portion thereof can be directed to a distillation column to separate the solvent from the off-gas so that it may be recycled. Passing through the distillation column, the off-gas is cooled while contacting internal packing materials or trays. This cooling allows the lower boiling point components, such as water, to be removed from the top of the column, while the higher boiling point components are returned to the bottom of the column and can be re-used, for example as solvent for the oxidation reaction. The cooling is typically assisted by introduction of a reflux at the top of the distillation column. This reflux typically comprises a liquid stream (preferably aqueous) containing materials which are the same as, or compatible with, the components of the oxidation process. Examples of such a liquid stream comprise water condensed from the distillation overhead gas, or from a predominantly water stream obtained by first condensing oxidation reactor off-gas to separate carboxylic acid solvent and subsequently condensing a portion of a resulting gas stream or, in processes in which oxidation and purification steps are integrated, a purification mother liquor resulting from the separation of a purification liquid stream from purified aromatic acid product or product and soluble purification by-products. Using such a purification mother or other liquid streams which may contain dissolved iron due to contact with equipment surfaces composed of iron or steel in the reflux may contribute to the formation of solid iron oxides on the surface of the internal packing materials of the distillation column.

The accumulation of iron oxides on packing materials comprising titanium is particularly undesirable. One publication has concluded that: "Accumulations of iron oxide . . . on titanium structured packing can promote or accelerate combustion of titanium. It may be appropriate to periodically remove accumulations of such materials through chemical or other means." (Centerline, Vol. 5, No. 2, Summer 2001, pp. 6–8, 15–18, published by Mary Kay O'Connor Process Safety Center). This publication further reports on a safety incident involving a fire at a chemical manufacturing facility, concluding that the presence of iron oxides "accelerated the oxidation of the titanium [packing materials] via a mechanism known as the Thermite Reaction in which the oxygen for combustion is taken from a less reactive metal oxide."

In U.S. Patent Application No. 60/327,464 filed Oct. 5, 2001, a cleaning process is proposed to remove accumulated iron oxides from the surface of aromatic acids manufacturing equipment exposed to liquid process streams which may carry dissolved iron. Nevertheless, it would be desirable to eliminate or decrease the need for cleaning by discovering a method of removing dissolved iron contamination from liquid streams during the aforementioned oxidation process and/or purification process.

SUMMARY OF THE INVENTION

In accordance with the invention, peroxide is added to an aromatic oxidation and/or purification liquid stream to cause the precipitation of dissolved iron contaminants which may be contained therein. By precipitation, amounts of dissolved iron contaminants which are present in liquid streams that pass through and come into contact with equipment are controlled or reduced, thereby controlling formation of iron oxides on the surfaces of such equipment. Further, the precipitated iron typically is present in amounts small enough that special measures are not required to remove it, though it may be separated from liquid streams by convenient means such as filtration. According to the invention, insoluble iron precipitates form instead of the surface formation of iron oxide on equipment. Accordingly, the invention may be used to increase the useful lifetime of equipment and decrease the need for iron oxide removal cleaning processes.

In one embodiment, the invention provides a process for making an aromatic carboxylic acid comprising steps which comprise contacting an oxidizable aromatic feed material with molecular oxygen in the presence of an oxidation catalyst and solvent in a liquid phase reaction mixture in a reactor under oxidation conditions to form a solid product comprising a crude aromatic carboxylic acid, a liquid comprising solvent and water, and an off-gas comprising vaporized water and vaporized solvent; separating a solid product comprising crude aromatic carboxylic acid from the liquid; directing at least a portion of the off-gas to a distillation column which is supplied with a reflux liquid to separate vaporized solvent from vaporized water such that a liquid stream comprising solvent and a distillation overhead gas comprising vaporized water are formed; returning to the reactor at least a portion of the liquid from the distillation column that comprises solvent; dissolving at least a portion of the separated solid product comprising crude aromatic carboxylic acid in a purification solvent to form a liquid purification solution; contacting the liquid purification solution with hydrogen in the presence of a hydrogenation catalyst and under hydrogenation conditions effective to form a liquid solution comprising purified aromatic carboxylic acid and purification solvent; separating solid purified aromatic carboxylic acid from the liquid remaining after purification; recycling at least a portion of the liquid remaining after separation of the solid purified aromatic carboxylic acid to at least one of the distillation step and the step comprising formation of the purification solution; and adding at least one peroxide to a liquid in or resulting from one or more of the other steps. In a preferred embodiment of the invention, the process includes a further step comprising recycling to the liquid phase reaction mixture in the reactor at least a portion of the liquid remaining after separation of the crude aromatic carboxylic acid. Addition of peroxide to a liquid present or produced in one or more steps of the process affords control over amounts of dissolved iron that may be present in such liquids and downstream process liquids that contain or are generated therefrom, such that deposition of solid iron oxide deposits on equipment surfaces is prevented or reduced.

Although not intending to be limited by any particular theory, it is thought that the dissolved iron in aromatic oxidation and/or purification liquid streams is dissolved iron(II). When a liquid stream is treated with peroxide, it is believed that the peroxide oxidizes the dissolved iron(II) and forms iron(III) hydroxide precipitates.

The addition of peroxide causes the precipitation of dissolved iron even in the presence of other dissolved metals typically present in an aromatic oxidation and/or purification liquid stream. It is surprising that dissolved iron is precipitated by a peroxide while other metals, such as oxidation catalyst metals which may be present in even greater amounts, are substantially not precipitated.

In accordance with the invention, an aromatic oxidation and/or purification liquid stream to be treated with peroxide may comprise dissolved metals other than iron. Specifically, dissolved non-iron metals are typically present in an aromatic oxidation and/or purification liquid stream as a result of oxidation catalyst metals used for the formation of crude aromatic acid. These dissolved non-iron metals typically include dissolved cobalt and/or manganese as these tend to be used commonly in commercial aromatic acid oxidation process steps, although other dissolved catalyst metals may be present in addition to or instead of these. For example, the typical amount of dissolved non-iron in an aromatic oxidation and/or purification liquid stream can range from 10–100 ppm or more. The amount of dissolved cobalt and/or manganese present in an aromatic oxidation and/or purification liquid stream can typically range from 10–100 ppm or more. The amount of dissolved iron present in an aromatic oxidation and/or purification liquid stream can typically range from 0.1 to 10 ppm or more. Because peroxide does not cause substantial precipitation of dissolved oxidation catalyst metals (e.g. cobalt and/or manganese), the potential for recycling these catalyst metals, e.g. by recycling oxidation mother liquor, is preserved.

It has also been surprisingly found that the addition of peroxide causes the precipitation of dissolved iron, even when larger quantities of terephthalic acid and/or oxidizable organic impurities, such as para-toluic acid, are present in an aromatic oxidation and/or purification liquid stream. The amount of terephthalic and/or oxidizable impurities in a liquid stream is variable and dependent on various factors including temperature, specific components of a given liquid stream, and specific oxidation conditions employed. For example, terephthalic acid is typically present in such liquid streams in substantial amounts and oxidation intermediates such as para-toluic acid and benzoic acid can also be present in appreciable amounts. Although these amounts typically are considerably greater than the amounts of dissolved iron species present as a result of contact of liquid process streams with surfaces of equipment constructed from steel or other sources of iron, and can lead to competing reactions with peroxide added for removal of dissolved iron, substantial precipitation of the iron is achieved even in the presence of such greater amounts of organic products and intermediates.

Peroxides suitable for use in the invention are those having the general formula $R_1$—O—O—$R_2$, wherein $R_1$ and $R_2$ are the same or different, and are hydrogen or a hydrocarbyl group. Due, at least in part, to its relatively low cost, the most preferred peroxide is hydrogen peroxide. To promote precipitation of dissolved iron, an excess amount of peroxide is preferably added to a liquid product, intermediate or process stream or portion thereof. For example, the peroxide is preferably added in molar excess with respect to the amount of dissolved iron present in an oxidation or purification mother liquor or other liquid process stream to which it is added. The amount of dissolved iron in a liquid stream may be determined by ICP (Inductively Coupled Plasma Spectroscopy).

It has also been surprisingly discovered that peroxide is capable of precipitating dissolved iron when added to an aromatic oxidation and/or purification liquid stream at elevated temperatures, e.g. at or greater than 200° F. (93° C.). For example, the peroxide may be added to a purification mother liquor with a temperature greater than 200° F. (93° C.) and cause the precipitation of dissolved iron therein. Peroxides tend to be easily degradable. As an example, hydrogen peroxide ($H_2O_2$) degrades to hydrogen gas and water. If left at room temperature for one year, about one-half of an amount of hydrogen peroxide would degrade. The rate of peroxide degradation increases with increasing temperature. Thus, it is surprising that peroxide added to an aromatic oxidation and/or purification liquid stream at elevated temperatures does not degrade before having an opportunity to precipitate dissolved iron.

In an embodiment of the invention, peroxide is added to a liquid stream during the manufacture of a crude aromatic acid. Crude aromatic acid is typically manufactured by oxidation of an oxidizable feedstock (e.g. ortho-xylene, meta-xylene, para-xylene, 1,5 dimethylnaphthalene, 2,6 dimethylnaphthalene) in an oxidation reactor in the presence of a carboxylic acid solvent, oxidation catalyst, and a source of oxygen. The catalyst used in the oxidation process is typically one that comprises one or more oxidation catalyst metals, which generally include those metals having an atomic number of about 21 to about 82. Typically, the pressure during the oxidation reaction is that pressure effective to keep the oxidizable feedstock and at least 70 percent of the solvent substantially in the liquid phase. Typical reaction gauge pressures in the oxidation reactor are in the range of from 0 kPa to 3430 kPa, and preferably are in the range of from 981 kPa to 2940 kPa. The temperature range within the oxidation reactor is typically from 120° C. to 240° C., and preferably from 150° C. to 230° C.

The oxidation reaction typically results in an oxidation slurry comprising precipitated crude aromatic acid and an oxidation liquid stream. These are commonly separated using a solid-liquid separation apparatus (e.g. centrifuge or filtration device such as a vacuum filter or pressure filter). At least a portion of this separated oxidation liquid stream (also known as oxidation mother liquor), which typically comprises one or more of the oxidation solvent, unreacted feed material, partially oxidized reaction by-products and catalyst, is preferably recycled to the oxidation reactor. In a specific embodiment of the invention, peroxide is added to the oxidation liquid stream prior to recycling of oxidation mother liquor, thereby causing the precipitation of dissolved iron. In this manner, dissolved iron contamination is decreased in the mother liquor recycle. Preferably, peroxide is added to the oxidation liquid stream before it is directed to a solid-liquid separation apparatus. In this manner, dissolved iron is precipitated from the oxidation liquid stream. Precipitated iron may be removed from the oxidation liquid stream using a solid-liquid separation apparatus added for the purpose of removing solid iron or may simply be circulated through the process such that it is removed in whole or in part in other solid-liquid separations included in the process.

The oxidation reaction for making a crude aromatic acid also typically results in the formation of an off-gas comprising vaporized solvent and vaporized water. To decrease solvent loss, all or part of the off-gas can be directed to a distillation column supplied with reflux liquid so that a gaseous phase comprising lower boiling point materials such as water are removed from the top of the column, while a liquid phase of higher boiling point materials such as solvent are returned to the reactor from the bottom of the column. In a specific embodiment of the invention, peroxide is added to the liquid utilized as reflux before it is supplied to a distillation column used to treat the off-gas from an oxidation reaction for making crude aromatic acid. In this manner, dissolved iron contaminants are removed from the reflux by precipitation, thereby decreasing the possibility of iron oxide formation on internal packing materials and other interior surfaces of the distillation apparatus.

In another embodiment of the invention, peroxide is added to a liquid stream during an aromatic acid purification process. Preferably, peroxide is added to a purification liquid stream during an aromatic acid purification process. Such a process comprises the hydrogenation of dissolved crude aromatic acid within a purification liquid stream to produce dissolved purified aromatic acid. Hydrogenation reaction temperatures and pressures are chosen so that the crude aromatic acid remains dissolved in the purification liquid stream. Typical reactor temperatures range from 450–600° F. (232–316° C.). Typical reactor pressure during hydrogenation may be in the range of 900 to 1500 pounds per square inch gauge (6205–10340 kPa), and usually is in the range of 900 to 1,300 pounds per square inch gauge (6205–8963 kPa).

After hydrogenation, temperature and pressure of the liquid purification stream containing dissolved, purified aromatic acid are lowered, causing crystallization of purified aromatic acid, which may be separated from the purification liquid stream, typically by filtration. The peroxide may be suitably added prior to filtration or other solid-liquid separation used to recover the crystallized, purified acid from the liquid, so that precipitated iron may be separated from the purification liquid stream. Alternatively, peroxide can be added to the purification mother liquor after the solid-liquid separation step, with the added benefit of reducing the presence of precipitated iron solids in the purified aromatic acid that is recovered. The resulting purification liquid stream in either such case, also known as purification mother liquor as noted previously, has lowered amounts of dissolved iron. All or part of such a purification mother liquor with decreased dissolved iron contaminations may be advantageously be used in a reflux for a distillation column used to separate reaction solvent from the off-gas produced in the oxidation reaction for producing a crude aromatic acid. Lowering dissolved iron contamination in this manner is particularly advantageous because the internal packing materials of such a distillation column are particularly susceptible to surface formation of iron oxides due to the presence of molecular oxygen in the oxidation reactor off-gas. By precipitating iron oxides from purification mother liquor before the purification mother liquor is used in a reflux for such a distillation column, the surface formation of iron oxides on the distillation column's internal packing materials may be decreased.

BRIEF DESCRIPTION OF THE DRAWING

The drawing depicts embodiments of the invention in relation to an integrated aromatic acid oxidation and purification process.

DETAILED DESCRIPTION OF THE INVENTION

In accordance with the invention, peroxide is added to an aromatic acid oxidation and/or purification liquid stream or a portion thereof to precipitate dissolved iron contaminants which may be present therein and thereby decrease the surface formation of iron oxides on equipment exposed to such liquid streams. Exposure of a liquid stream to iron containing surfaces of equipment used during aromatic oxidation and/or purification can result in contamination of the liquid stream with dissolved iron. Peroxide is preferably added to a liquid stream after the liquid stream has been exposed to such iron containing surfaces. The resulting treated liquid stream has lowered amounts of dissolved iron contamination as compared to dissolved iron that is present in the streams before being treated with peroxide. Accordingly, it is preferable that peroxide is added to a liquid stream so that further exposure of the resulting treated liquid stream with iron containing surfaces is decreased. More preferably, peroxide is added to a liquid stream after it has been exposed to a majority or substantial portion of the total amount of iron containing surfaces of equipment used during an aromatic oxidation and/or purification process. Preferred examples of where a liquid stream has been exposed to a majority of the total amount of iron containing surfaces during an aromatic oxidation and/or purification process is immediately before or after a solid-liquid separation step thereof. As will be appreciated, peroxide can be introduced into one or more liquid streams at one or more points of the process and, in continuous processes, peroxide can be added continuously or intermittently as desired. A metering pump or similar device capable of delivering peroxide at a given rate directly to process transfer lines or vessels or to a transfer line in communication with such a process line or vessel is most conveniently used for introduction of peroxide into process liquids.

The amount of peroxide added to a liquid stream is any amount that causes the precipitation of dissolved iron therein. Amounts effective to reduce presence of dissolved iron species are well in excess of amounts that interfere with process operability and effectiveness in other respects. In a specific embodiment, precipitation is promoted by adding peroxide to the aromatic oxidation and/or purification liquid stream in molar excess of the dissolved iron in the liquid stream. The amount of dissolved iron may be determined by ICP (Inductively Coupled Plasma Spectroscopy). Preferably, peroxide should not be added in an amount to cause the substantial precipitation of dissolved catalyst metals (e.g. cobalt and manganese) in a liquid stream. Preferably, the amount of peroxide does not exceed impractical amounts. For example, an ordinary artisan may easily determine when increasing the amount of peroxide has little or no effect upon the precipitation of iron. Preferably, the molar ratio of peroxide to dissolved iron is at least 10:1, more preferably at least 25:1, still more preferably at least 50:1, and still more preferably at least 100:1. For dissolved iron and catalyst metal contents of typical large scale aromatic acid oxidation and purification steps, molar ratios in the range of about 5:1 to 100:1 are well suited for precipitating iron compounds without substantial loss of catalyst metals to precipitation, with ratios of about 10:1 to 50:1 being particularly suited when peroxide is added to a dissolved aromatic acid to be purified or a purification mother liquor after separation of the purified acid due to the reduced levels of dissolved catalyst metals in purification as compared to their levels in liquid streams present in or resulting from process steps such as oxidation, separation of aromatic carboxylic acid from the oxidation liquid reaction mixture and recycle of oxidation mother liquor.

Preferred amounts of peroxide to be added to a liquid stream may also be described in relation to the space velocity or throughput of the liquid stream at the point of addition of peroxide. In this regard, peroxide is preferably added in an amount of 1–100 grams of peroxide per 1000 kg of liquid stream to provide adequate peroxide for precipitation of iron without substantial formation of catalyst metal solids, although greater amounts, for example up to 250 grams peroxide per 1000 kg liquid stream are generally suitable and especially in the case of peroxides such as hydrogen peroxide, lower alkyl peroxides and benzoyl peroxide, which are or decompose into products that are compatible with other components used and generated during oxidation or purification.

The amount of dissolved iron in a given liquid stream may vary and depends on several factors such as the corrosivity and location of the liquid stream within the overall aromatic oxidation and/or purification process. For example, amounts of dissolved iron typically range up to about 10 ppm. However, amounts as low as 0.5 ppm may be detrimental. The invention can be made effective for any level of dissolved iron that is or may be present in a liquid stream by adjusting the amount of peroxide added to the liquid stream depending upon the levels of dissolved iron as determined by analysis.

After treating a liquid stream by addition of peroxide to precipitate dissolved iron, the resulting liquid stream contains decreased amounts of dissolved iron. Preferably, a treated liquid stream comprises no more than 6 ppm, preferably no more than 3 ppm, and most preferably no more than 0.5 ppm of dissolved iron. After addition of a peroxide the amount of dissolved iron is preferably removed in amounts of at least 40 wt %, more preferably at least 70 wt %, more preferably at least 85 wt %, and most preferably at least 95 wt % of the amount of dissolved iron present before peroxide addition.

Various non-iron metals are used as oxidation catalysts for producing crude aromatic carboxylic acids, and result in aromatic oxidation and/or purification liquid streams having amounts of these catalyst metals dissolved therein. Despite the presence of such catalyst metals, peroxide may nevertheless be surprisingly used to remove dissolved iron by precipitation. Dissolved catalyst metals are typically present in greater amounts than dissolved iron in some liquid streams, and especially oxidation liquid streams and mother liquors. Surprisingly, these dissolved non-iron metals do not interfere with the peroxide's precipitation of the dissolved iron. For example, in some aromatic oxidation and/or purification liquid streams, the weight ratio of dissolved non-iron metals to dissolved iron may range from 25:1 to 100:1 or higher. The weight ratio of dissolved cobalt to dissolved iron in some aromatic oxidation and/or purification liquid streams can range from 5:1 to 50:1 or higher and the weight ratio of dissolved manganese to dissolved iron can range from 5:1 to 50:1 or higher. The amount of dissolved cobalt, manganese and other catalyst metals present in an aromatic oxidation and/or purification liquid stream typically ranges from 1–50 ppm or higher for each such metal. An advantageous aspect of the invention is that peroxide does not substantially cause the precipitation and subsequent removal of dissolved oxidation catalyst metals in an aromatic oxidation and/or purification process stream. These dissolved oxidation catalyst metals are preferably present in a liquid stream after the liquid stream is treated with peroxide to preserve the re-use of catalyst metals. Dissolved catalyst metals present in an aromatic oxidation and/or purification liquid stream are preferably removed in an amount no more than 30 wt %, preferably no more than 20 wt %, and more preferably no more than 10 wt % of the amounts of such metals present in solution in a process liquid prior to its being treated with peroxide to remove dissolved iron that may be present. Dissolved cobalt is preferably removed in an amount no greater than 15 wt %, preferably no greater than 10 wt %, and most preferably no greater than 5 wt %. Dissolved manganese in an aromatic oxidation and/or purification liquid stream is preferably removed in an amount no greater than 15 wt %, preferably no greater than 10 wt %, and most preferably no greater than 5 wt %. As will be appreciated, substantial retention of dissolved oxidation catalyst metals in a liquid stream is particularly desirable in the case of oxidation mother liquor and other liquids to be recycled to oxidation.

This invention is particularly suitable for use in an oxidation process for making crude terephthalic acid and/or an aromatic acid purification process for purifying crude terephthalic acid. Typically, the manufacture of crude terephthalic acid involves the catalytic oxidation of para-xylene to form crude terephthalic acid product that may also comprise partially oxidized by-products such as p-toluic acid and 4-carboxybenzaldehyde. In the invention, peroxide is used to precipitate or control amounts of dissolved iron from a mother liquor which typically comprises substantial levels of terephthalic acid as well as oxidizable organic impurities which are typically present in far greater amounts than amounts of dissolved iron, but surprisingly, do not interfere with the peroxide's precipitation of the dissolved iron. For example, in a typical liquid stream, the weight ratio of oxidizable organic impurities to dissolved iron can range up to 50,000:1, with oxidation liquid streams typically having considerably greater ratios, e.g., 1000:1 or greater, than purification liquid streams, e.g., 100:1 to 10000:1.

Peroxides suitable for use in the invention are those having the general formula $R_1$—O—O—$R_2$; wherein $R_1$ and $R_2$ are the same or different, and are hydrogen or a hydrocarbyl group. Preferred peroxides are those wherein $R_1$ and $R_2$ in the formula are the same or different and are chosen from hydrogen, a $C_1$–$C_8$ alkyl, $C_1$–$C_8$ alkenyl, $C_1$–$C_8$ alkynyl, $C_6$–$C_{12}$ acyl, benzoyl and lower alkyl ($C_{1-4}$)-substituted benzoyl. Combinations of two or more peroxides may be used, with introduction of the combined materials at one or more given locations in the process or of each at different locations being suitable. Examples of peroxides suitable for use in the invention are hydrogen peroxide, di-t-butyl peroxide, di-benzoyl peroxide, t-butyl hydro peroxide. Due, at least in part, to its relatively low cost and ease of handling, the most preferable peroxide is hydrogen peroxide.

Peroxides used according to the invention preferably are relatively pure, such as those commercially available as chemical or food application grade peroxides. Preferably, purity is such that sulfate impurities are present in amounts of 500 ppm or less, and more preferably less than about 100 ppm. More pure forms, such as those used in semiconductor manufacture, can be utilized if desired, although the additional purity may not lead to enhanced performance in the present invention. Less pure grades may contain impurities, such as sulfates, in undesirably high levels. For use according to the invention, peroxide preferably is used as a solution in water or other solvent compatible with the aromatic acid and/or purification process(es) to facilitate handling and avoid corrosion of equipment, such as reservoirs, pumps and transfer lines used for storing and adding peroxide to process streams. Peroxide concentrations ranging from 0.1 to 70 wt % are generally preferred when peroxide is used in solution, with specific concentrations varying with point or points of addition to the process, integration of equipment to be used for the addition with other process equipment, choice of peroxide and other considerations, as will be apparent to persons skilled in the art.

Because peroxide degradation increases with increasing temperature, it is surprising to discover that a peroxide is capable of precipitating dissolved iron instead of degrading when added to an aromatic oxidation and/or purification stream having a high temperature, e.g. greater than 200° F. (93° C.). In the invention, peroxide is capable of effectively precipitating dissolved iron in an aromatic oxidation and/or purification stream at temperatures greater than 200° F. (93° C.) or 300° F. (149° C.). However, the peroxide is added to an aromatic oxidation and/or purification stream at a temperature low enough such that the peroxide causes the precipitation of dissolved iron therein before the peroxide degrades. Accordingly, it is preferred to add peroxide to a mother liquor or other liquid stream at a temperature of no more than 500° F. (260° C.), and more preferably no more than 400° F. (204° C.).

In an embodiment of the invention, peroxide is added to purification liquid stream during an aromatic acid purification process which involves the hydrogenation of a crude aromatic acid. This invention is applicable to any aromatic acid purification process, such as those known in the art, examples of which are described in U.S. Pat. Nos. 5,354,898 and 5,362,908, both of which are incorporated by reference. In general, an aromatic acid purification process comprises the hydrogenation of dissolved crude aromatic acid within a purification liquid stream comprising solvent to produce dissolved purified aromatic acid. The dissolved purified aromatic acid is then crystallized and the resulting solid, purified acid separated from the purification liquid stream, typically by filtration. Peroxide may be added to a purification liquid stream anywhere in an aromatic acid purification process, but to avoid the high temperature of hydrogenation, peroxide is preferably added after hydrogenation. Peroxide may be added after crystallization, but before separation (e.g. filtration), so that precipitated iron may be separated from a purification liquid stream along with purified aromatic acid. Alternatively, peroxide is added after separation of crystallized, purified aromatic acid to a liquid purification mother liquor that is recycled in whole or in part. Most preferably, peroxide is added to such a purification mother liquor after separation of the purified aromatic acid and the resulting stream is recycled for use as reflux liquid in distillation of an off-gas from an aromatic acid oxidation reactor.

The invention may be suitably used in an aromatic acid purification process, wherein crude aromatic acid (e.g. crude terephthalic acid) is dissolved in a purification liquid stream comprising solvent and treated with hydrogen in a pressure reactor vessel in a first reaction zone containing a hydrogenation catalyst. The hydrogenation catalyst of the pressure reactor vessel typically comprises one or more active hydrogenation catalyst components supported on a carrier material. The carrier material is typically in a granular form, although pellets or other types of particulate forms may be used. When in a granular form, the granules preferably have an average size of −2 mesh to −12 mesh (U.S. Sieve Series), more preferably −4 mesh to −8 mesh. The carrier material is preferably an active carbon, and is more preferably derived from coconut charcoal. Such active carbon typically has a surface area of at least 600 m$^2$/gram (N$_2$, BET Method), preferably 800 m$^2$/gram to 1500 m$^2$/gram. While active carbon derived from coconut charcoal in the form of granules is preferred as a support material for the hydrogenation catalyst component, other porous carbonaceous, metal oxide or other supports or substrates may be used.

The hydrogenation catalyst contains at least one active catalytic hydrogenation component. Particularly suitable catalytic hydrogenation components are the Group VIII metals of the Periodic Table of Elements (IUPAC version), including palladium, platinum, rhodium, osmium, ruthenium, iridium, and mixtures thereof. The catalytic hydrogenation catalyst component may be deposited on, or added to, the carbon or other carrier material by any suitable method, for example, by treating the carrier with a solution of one or more soluble Group VIII metal compounds, such as palladium chloride, and then drying the result to remove excess solvent.

A preferred loading of the Group VIII metal on the carrier is in the range of 0.01 to 2 wt % based on the total weight of the finished catalyst, i.e. the total weight being the weight of the dry carbon carrier and the active hydrogenation component. More preferably, the Group VIII metal loading on the carbon carrier is 0.2 to 0.8 wt %.

Suitable catalysts and catalyst beds useful in the embodiment of this invention relating to aromatic acid purification are described, for example, in U.S. Pat. Nos. 4,394,299; 4,629,715; 4,728,630 and 4,892,972. A suitable palladium-on-carbon catalyst may be obtained, for example, from Engelhard Corporation, Edison, N.J., Also, suitable rhodium-on-carbon catalysts may be obtained from Engelhard Corporation.

A suitable reactor for hydrogenation is any reactor vessel that can withstand the temperature and pressure used for the hydrogenation of a crude aromatic acid dissolved in purification solvent. The preferred reactor configuration is a cylindrical reactor positioned with its axis vertically disposed and having the hydrogenation catalyst contained therein in a fixed bed. In the preferred mode of operation, crude aromatic acid dissolved in a purification solvent is added to the reactor vessel at a position at or near the top portion of the reactor vessel, and the crude aromatic acid dissolved in the purification liquid stream flows down through the bed of hydrogenation catalyst contained in the reactor vessel in the presence of hydrogen gas, wherein impurities are reacted with hydrogen gas. In this preferred mode, the crude aromatic acid is purified and the purified product is removed from the reactor vessel at a position at or near the bottom of the reactor.

In a suitable reactor vessel apparatus, a hydrogenation catalyst preferably comprising a carbon carrier and an active hydrogenation catalyst component supported on the carrier is held within the reactor vessel by a screen or other means that retains the catalyst particles in the reactor, yet allows the relatively free passage of crude aromatic acid dissolved in the purification liquid stream. The means used for retaining the catalyst particles may be a flat mesh screen or a screen made by closely spaced parallel wires. Other suitable catalyst retaining means include, for example, a tubular Johnson screen or a perforated plate. The means used for retaining the catalyst particles is constructed of a material that is suitably resistant to corrosion and is of an appropriate strength to efficiently retain the catalyst bed. Most suitably, the means used for retaining the catalyst bed has openings of 1 mm or less and is constructed of a metal such as stainless steel, titanium or Hastelloy C.

The reactor may be operated in several modes. For example, a predetermined liquid level may be maintained in the reactor and hydrogen may be fed in, for any given reactor pressure, at a rate sufficient to maintain the predetermined liquid level. The difference between the actual reactor pressure and the vapor pressure of purification liquid stream present is the hydrogen partial pressure in the reactor vapor space. Alternatively, if hydrogen is fed in admixture with an inert gas such as nitrogen, the difference between the actual reactor pressure and the vapor pressure of the crude acid solution present is the combined partial pressure of hydrogen and the inert gas admixed therewith. In this case the hydrogen partial pressure may be calculated from the known relative amounts of hydrogen and inert gas present in the admixture. In yet another operating mode, the reactor may be filled with a purification liquid stream so as to provide no reactor vapor space. That is, the reactor may be operated as a hydraulically full system with dissolved hydrogen being fed to the reactor by flow control. In such an instance, the concentration of hydrogen in solution may be modulated by adjusting the hydrogen flow rate to the reactor. If desired, a pseudo-hydrogen partial pressure value may be calculated from the solution hydrogen concentration which, in turn, may be correlated with the hydrogen flow rate to the reactor.

In the operating mode where process control is effected by adjusting the hydrogen partial pressure, the hydrogen partial pressure in the reactor is preferably in the range of 10 pounds per square inch gauge to 200 pounds per square inch gauge (69–1379 kPa) or higher, depending upon the service pressure rating of the reactor, the degree of contamination of the aforementioned crude aromatic acid, the activity and age of the particular catalyst employed, and other processing considerations known to persons skilled in the art. In the operating mode where process control is effected by directly adjusting the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, the amount of hydrogen to be supplied to the purification reactor under reaction conditions is, of course, sufficient to effect the desired hydrogenation.

The space velocity, reported as weight of the crude aromatic acid per weight of catalyst per hour, during hydrogenation is typically from 1 hour$^{-1}$ to 25 hour$^{-1}$, preferably from 2 hours$^{-1}$ to 15 hours$^{-1}$. The residence time of the purification liquid stream in the catalyst bed varies, depending upon the space velocity.

After hydrogenation, the hydrogenated stream, now comprising purified aromatic acid and solvent, is removed from the reactor and cooled to a crystallization temperature. The crystallization temperature is sufficiently low (e.g. 160° C. or below) for crystallization of the purified aromatic acid to occur, thereby producing crystals within the liquid phase. The crystallization temperature is sufficiently high so that impurities and their reduction products (products resulting from hydrogenation) remain dissolved in the liquid phase. Thereafter, the liquid, containing dissolved impurities and their reduction products, is separated (typically by filtration) from the crystallized purified aromatic acid. Peroxide is preferably added to the liquid product after crystallization to avoid the high temperatures during hydrogenation. Upon addition of the peroxide, an iron precipitate is formed which may then be separated (e.g. filtered) from the liquid along with the crystallized purified aromatic acid.

As already set forth, iron oxide may be detrimental when formed upon titanium surfaces of equipment because of such equipment's exposure to an aromatic oxidation and/or purification liquid stream contaminated by dissolved iron. Accordingly, it is preferable to add peroxide to a liquid stream to precipitate dissolved iron before it contacts the titanium surfaces of equipment. For example, peroxide is preferably added to reflux before it is supplied to a distillation column used during an aromatic oxidation process. In certain processes, such as those which integrate aromatic oxidation and purification, the reflux liquid may comprise a purification liquid stream (e.g. purification mother liquor) as a component. The invention may be used to precipitate or control levels of dissolved iron contaminants in a purification liquid stream or portion thereof before it is introduced as a component for distillation column reflux.

During an aromatic oxidation process, distillation columns are typically used to separate lower boiling point components (e.g. water) from higher boiling point components (e.g. reaction solvent). Specifically, a distillation column may be used in an aromatic oxidation process comprising introducing a feedstock (e.g. paraxylene) to a reactor in the presence of a carboxylic acid solvent, an oxidation catalyst, and a source of molecular oxygen (typically air). An exothermic oxidation occurs in the reactor to produce a crude aromatic acid and an off-gas which exits the reactor. This off-gas comprises vaporized aliphatic carboxylic acid, vaporized water (a reaction by-product), and molecular oxygen. All or a portion of the off-gas is directed to the bottom of a distillation column while reflux is added at the top of the column to cool the off-gas as it rises in the column and contacts the internal packing materials or trays of the distillation column. As the off-gas cools, its higher boiling point components, such as carboxylic acid oxidation solvent, migrate to the bottom of the column and may be returned, at least in part, to the reactor. Lower boiling point components, such as water, migrate to the top of the column where they may be removed. Thus a distillation column facilitates solvent recycling and simultaneously facilitates removal of water, a by-product of the oxidation reaction. Examples of distillation columns employed in this manner are U.S. Pat. Nos. 5,612,007 and 5,723,656, both of which are hereby incorporated by reference. High pressure steam or other overhead gas from distillation can provide a source of energy that can be recovered, such as with an expander. Another example of a process using a distillation column for treating aromatic oxidation reactor off-gas and with condensation of a portion of the distillation column overhead gas and return of the condensate to the distillation column as reflux is described in U.S. Pat. No. 6,504,051, which is also incorporated herein by reference.

Because the off-gas that comes in contact with the reflux comprises molecular oxygen, it is particularly important to decrease the amount of dissolved iron in the reflux to prevent its oxidation and the resulting surface formation of iron oxide on the internals of the distillation column. This may be accomplished by adding peroxide to the components of the reflux liquid and/or the reflux itself and allowing dissolved iron to sufficiently precipitate before the reflux is supplied to a distillation column. The length of time for sufficient precipitation (i.e. residence time) depends on various factors including the amount of dissolved iron to be precipitated. Typical residence time ranges from 5–30 seconds.

Specific embodiments of the invention may be understood by reference to the drawing, which depicts an example of an integrated process comprising aromatic oxidation and aromatic acid purification process steps. The aromatic oxidation process step begins with a stirred tank reactor (10) while the purification process begins with a slurry vessel (110).

With respect to the aromatic oxidation process, starting materials (not shown) are introduced to a reactor (10). These starting materials include feedstock, solvent, catalyst, and oxygen. The feedstock comprises an aromatic compound substituted with at least one oxidizable group such as an alkyl or acyl group or combinations thereof. Typical feedstocks suitable for oxidation to form aromatic acids include ortho-xylene, meta-xylene, para-xylene, 1,5 dimethylnaphthalene, 2,6 dimethylnaphthalene, and the like. The solvent may be any aliphatic or aromatic carboxylic acid and preferably comprises a C2–C5 aliphatic carboxylic acid, more preferably acetic acid. The catalyst typically comprises cobalt, manganese, and bromine. A suitable source of oxygen is air, although pure oxygen, oxygen-enriched air and other suitable oxygen-containing gases can be used. In the presence of solvent, catalyst and oxygen, the feedstock is oxidized in a liquid phase reaction mixture to form a corresponding crude aromatic acid product. For example, para-xylene is oxidized to form a crude terephthalic acid product. A portion of the crude aromatic acid product formed by oxidation precipitates from the liquid reaction mixture, thereby forming a slurry with a solid phase comprising the crude aromatic acid product and an oxidation liquid stream comprising solvent, water and unreacted feed material. The oxidation reaction is conducted under conditions that result in formation of a reactor off-gas that comprises water and vaporized solvent, typically with unconsumed oxygen, inert gases from the oxygen source and gaseous reaction by-products also present. The off-gas is removed from the vapor space in the reactor to distillation column (20) via line (12).

Slurry from oxidation reactor (10) is introduced into a crystallizer vessel (120) wherein temperature and pressure are reduced and additional aromatic acid product is precipitated from the liquid phase. This slurry is preferably directed to additional crystallizer vessels (not shown) connected in series wherein temperatures and pressures are gradually reduced in each successive vessel. Such a gradual reduction of pressure and temperature allows for more efficient precipitation of the crude aromatic acid product. After the slurry is reduced to an appropriate temperature and pressure, it is directed to solid-liquid separation (135) via line (128), wherein crude aromatic acid product is separated from the oxidation liquid stream. This separated oxidation liquid stream is also known as "oxidation mother liquor." Although any suitable device for separating solids from liquids is useful for solid-liquid separation (135), use of a centrifuge or filtration device, such as a rotary vacuum filter or pressure filter is preferred.

After solid-liquid separation (135), at least a portion of oxidation mother liquor may be recycled via line (145) and returned to the reactor (10), while the crude aromatic acid product is directed via line (136) to slurry vessel (110) to begin the purification process. The solid phase comprising the crude aromatic acid product may optionally be dried and/or stored before beginning the purification process. In the slurry vessel (110), the crude aromatic acid product is mixed with water supplied from line (105) and then directed to a hydrogenation reactor (160) where the crude aromatic acid product is dissolved in water and treated with hydrogen at an elevated temperature and pressure. Effluent from the hydrogenation reactor (160) is directed to a crystallization vessel (170) wherein temperature and pressure are reduced allowing purified aromatic acid to precipitate. Accordingly, a slurry is formed in the crystallization vessel (170) having a solid phase comprising purified aromatic acid, and a purification liquid stream comprising water and un-precipitated acid. This slurry is preferably directed to additional crystallizer vessels (not shown) connected in series wherein temperature and pressure are gradually reduced in each successive vessel. Such a gradual reduction of pressure and temperature allows for more efficient precipitation of the purified aromatic acid product.

After the slurry is reduced to an appropriate temperature and pressure, it is directed to a solid-liquid separation apparatus (180) wherein the purified aromatic acid product is separated from the purification liquid stream. The separated purification liquid stream is also known as "purification mother liquor." Although any suitable device for separating solids from liquids can be used for solid-liquid separation (180), use of a centrifuge or filter apparatus is preferred.

Throughout the oxidation and purification process depicted by FIG. 1, various liquid streams may come into contact with iron-containing equipment (e.g. stainless steel), thereby resulting in the presence of dissolved iron contaminants in such liquid streams. For example, the liquid transfer lines depicted as 115, 128, 145, 158, 165, 175, and 200 may have surfaces comprising iron-containing materials (e.g. stainless steel), which contact liquid streams passing through such lines. Furthermore, vessels depicted as 110, 160, 170, and 180 may have surfaces comprising iron-containing materials (e.g. stainless steel) which contact liquid streams processed in or passing through such equipment. Dissolved iron contamination may result in the formation of iron oxide deposits on various pieces of equipment and feed lines depicted in FIG. 1.

In accordance with the invention, the formation of iron oxide deposits upon the surfaces of equipment is decreased or controlled by adding peroxide to an aromatic oxidation and/or purification liquid stream, thereby precipitating dissolved iron therein. More preferably, to increase dissolved iron removed via precipitation, the peroxide is added to a liquid stream in an amount of time (i.e. residence time) before the liquid stream is directed to solid-liquid separation, so as to cause sufficient precipitation of dissolved iron. Most preferably, precipitated iron is at least substantially removed from the liquid stream in such a solid-liquid separation step. Preferably, the peroxide is added upstream of solid-liquid separation. In another embodiment, peroxide is added at at least one point downstream from solid-liquid separation. If desired, removal of precipitated iron solids can be achieved by one or more filters or other solid-liquid separation devices within the process design or added for removal of iron solids. Residence time of peroxide in liquid process streams depends on various factors, including the amount of dissolved iron to be precipitated. Typical residence time is at least 5 seconds.

In reference to the drawing, peroxide (e.g. $H_2O_2$) is added, e.g. via line (215) and/or via line (228), before a liquid stream comprising a slurry of crude aromatic acid product is introduced to solid-liquid separation (135). Additionally or alternatively, peroxide is added (e.g. via line (265) and/or (275)), before a liquid stream slurried with purified aromatic acid product is introduced to solid-liquid separation (180).

In another embodiment of the invention, peroxide is added to a liquid stream which is used as reflux to the distillation column before the stream is directed to the column. Addition of the peroxide causes the precipitation of dissolved iron contained in the reflux liquid, thereby decreasing the amount of dissolved iron capable of forming iron oxide on the distillation column's internal structure, such as packing materials, when the reflux enters the distillation column. Preferably, to increase dissolved iron removed via precipitation, the peroxide is added to the reflux at least 5 seconds before the reflux is directed to a distillation column. Specifically, in reference to the drawing, peroxide is added via line (300) to a reflux carried by line (200) to a distillation column (20). In the embodiment shown in the drawing, the reflux to distillation column (20) comprises at least a portion of the purification mother liquor resulting after separation of purified aromatic acid in separation device (180). Because addition of the peroxide does not cause substantial precipitation of dissolved oxidation catalyst metals (e.g. cobalt and/or manganese), the recycling of these catalyst metals with oxidation solvent or solvent and water from the distillation column to the oxidation reactor via line (25) is not hampered while problems associated with iron oxide formation in the internal packing materials distillation column (20) are ameliorated.

The addition of peroxide to a liquid stream may be accomplished by any known method. For example, the peroxide may be pumped from a reservoir into a transfer line leading to a line containing a liquid stream. The reservoir is preferably kept at a temperature to prevent unacceptable degradation, e.g. temperatures between about 0° C. to about 50° C., preferably between about 0° C. to about 30° C. In reference to FIG. 1, peroxide may be pumped from a reservoir (not shown) into one or more of transfer lines 215, 228, 265, 275, and 300, which are respectively connected to, and direct peroxide into, lines 115, 128, 165, 175, and 200. While peroxide is suitably added to a process at essentially any convenient point in the process, depicted according to the drawing, it is preferably added to the liquid present or produced in one or more of the following steps of the process: separation of crude aromatic acid from the oxidation liquid stream; formation of the purification solution of crude aromatic acid in a purification solvent; separation of purified aromatic acid from the hydrogenation reaction mixture; or recycle of purification mother liquor.

EXAMPLES

In examples 1–4, hydrogen peroxide ($H_2O_2$) was added to a purification mother liquor to cause the precipitation of dissolved iron. For all of those examples, the purification mother liquor was obtained from the mother liquor of a terephthalic acid purification process. The terephthalic acid purification process was performed by hydrogenation of crude terephthalic acid dissolved in a purification solvent comprising water to make dissolved purified terephthalic acid, crystallizing the purified terephthalic acid, and separating the purified terephthalic acid from the purification solvent. The purification mother liquor used in examples 1–4 was the mother liquor after separation of the terephthalic acid. In Example 1, ICP (Inductively Coupled Plasma Spectroscopy) was performed using a Spectro Flame Compact S, available from Spectro Analytical UK Limited. In Examples 2–4, ICP was performed by a S.A. J.Y. Ultima spectrometer obtainable from Jobin Yvon Inc. of Edison, N.J.

Example 1

About 400 ml of purification mother liquor was heated to 80° C. and filtered. An analysis of the filtrate by ICP indicated about 0.47 ppm of iron. About 1 ml of 30 wt % aqueous peroxide was then added to the purification mother liquor. After about 10–15 seconds, a sample of the purification mother liquor was filtered, and an analysis of the filtrate indicated that the level of dissolved iron was lowered to 0.3 ppm. As shown by this Example, the amount of dissolved iron in a purification mother liquor decreased as a result of addition of a peroxide.

Example 2

Examples 2a and 2b were conducted to show that dissolved iron may be precipitated from a purification mother liquor even in the presence of a greater quantity of dissolved manganese (Mn), and at a temperature of 300° F. (149° C.).

For examples 2a–2b, purification mother liquor was filtered at room temperature to remove suspended terephthalic acid solids, and analyzed by ICP to determine amounts of dissolved metals prior to use. These examples employed a flow reactor apparatus to treat the purification mother liquor with hydrogen peroxide in a continuous manner. The apparatus consisted of a vertical titanium tube reactor (1-inch (2.54 cm) inner diameter, 12 inches (30.48 cm) long) packed with 3-mm glass beads. The reactor tube was heated by external electrical tracing to 300° F. (149° C.), as measured by internal thermocouples. The purification mother liquor was pumped from a reservoir into a main transfer line, connected to the reactor, and flowed through the reactor upflow at a rate of 1 liter/hour. No hydrogen peroxide was used in Example 2a. In Example 2b, a 25 mL/hour feed of 0.03 wt % hydrogen peroxide solution (aqueous) was pumped from a reservoir through a transfer line connected to the main transfer line before the reactor. The resulting combined purification mother liquor/hydrogen peroxide solution stream, containing 7.5 ppm hydrogen peroxide, passed through a short preheat line and then up the reactor tube at 185 psig (1274 kPa) and 300° F. (149° C.). Estimated residence time of the liquid in the reactor was about 5 minutes. The reactor effluent passed through a heat exchanger, a back-pressure regulator, and then to a sampling vessel, where liquid samples were collected periodically. The liquid samples were analyzed for dissolved metals by the ICP after filtration.

The results of Examples 2a and 2b, given in Table I, show the effectiveness of the hydrogen peroxide treatment for removal of iron (Fe) from the purification mother liquor, even in the presence of a larger amount manganese (Mn). In Example 2a, where no peroxide was used, a 10 wt % removal of dissolved Fe was achieved. It is believed that minor amounts of oxygen caused this nominal removal of Fe via oxidation and formation of iron oxide. In Example 2b, where peroxide was used, a 90 wt % removal of dissolved Fe was achieved.

TABLE I

| | Purification mother liquor (starting material) | Example 2a | Example 2b |
|---|---|---|---|
| $H_2O_2$ Employed? | — | no | yes |
| Dissolved Fe | 0.40 ppm* | 0.36 ppm** | 0.04 ppm*** |
| Fe Removal | — | 10 wt % | 90 wt % |
| Dissolved Mn | 51 ppm* | 52 ppm** | 49 ppm*** |
| Mn Removal | — | 0% | 4% |

*Average of 8 samples.
**Average of 2 samples collected over 4 to 5.5 hours on stream.
***Average of 3 samples collected over 5 to 23 hours on stream.

Example 3

Examples 3a and 3b were conducted to show that dissolved iron may be precipitated from a purification mother liquor even in the presence of greater quantities of dissolved cobalt (Co) and manganese (Mn), and at a temperature of 300° F. (149° C.)

For Examples 3a–3b, purification mother liquor was filtered at room temperature to remove suspended terephthalic acid solids, and analyzed by ICP to determine the amounts of dissolved metals prior to use. These Examples employed a flow reactor apparatus as in Example 2 to treat the purification mother liquor with hydrogen peroxide in a continuous manner. The purification mother liquor was flowed through the reactor upflow at a rate of 1 liter/hour. No hydrogen peroxide was used in Example 3a. In Example 3b, a 25 mL/hour feed of 0.03 wt % hydrogen peroxide solution (aqueous) was pumped from a reservoir through a transfer line connected to the main transfer line before the reactor. The resulting combined purification mother liquor/peroxide solution stream, containing 7.5 ppm hydrogen peroxide, passed through a short preheat line and then upflow through the reactor tube at 185 psig (1274 kPa) and 300° F. (149° C.). Estimated residence time of the liquid in the reactor was about 5 minutes. The reactor effluent passed through a heat exchanger, a back-pressure regulator, and then to a sampling vessel, where liquid samples were collected periodically. The liquid samples were analyzed for dissolved metals by ICP after filtration.

Results of these Examples 3a and 3b, given in Table II, show the effectiveness of the hydrogen peroxide treatment for removal of iron (Fe) from purification mother liquor, even in the presence of larger amounts of Co and Mn. In Example 3a, where no peroxide was used, a 28 wt % removal of dissolved Fe was achieved. It is believed that minor amounts of oxygen caused this nominal removal of Fe via oxidation and formation of iron oxide. In Example 3b, where peroxide was used, a 75 wt % removal of dissolved Fe was achieved.

TABLE II

| | Purification mother liquor (starting material) | Example 3a | Example 3b |
|---|---|---|---|
| $H_2O_2$ Employed? | — | no | yes |
| Dissolved Fe | 0.57 ppm | 0.41 ppm* | 0.14 ppm** |
| Fe Removal | — | 28% | 75% |
| Dissolved Mn | 32 ppm | 33 ppm* | 32 ppm** |
| Mn Removal | — | 0% | 0% |
| Dissolved Co | 12 ppm | 12 ppm* | 12 ppm** |
| Co Removal | — | 0% | 0% |

*Average of 3 samples collected over 2 to 4 hours on stream.
**Average of 4 samples collected over 2 to 8 hours on stream.

Example 4

Example 4 was conducted to show that dissolved iron may be precipitated from a purification mother liquor even in the presence of terephthalic acid and greater amounts of cobalt (Co) and manganese (Mn).

A purification mother liquor was filtered at room temperature to remove suspended terephthalic acid solids and analyzed by ICP to determine amounts of dissolved metals prior to use. Terephthalic acid was added to the filtered purification mother liquor to yield 0.1 wt % (1000 ppm) of suspended terephthalic acid in the purification mother liquor. This example employed a flow reactor apparatus as in Example 2 to treat the purification mother liquor with hydrogen peroxide in a continuous manner. The purification mother liquor was flowed through the reactor upflow at a rate of 1 liter/hour. In this Example, a 25 mL/hour feed of 0.03 wt % hydrogen peroxide solution (aqueous) was pumped from a reservoir through a transfer line connected to the main transfer line before the reactor. The resulting combined purification mother liquor/hydrogen peroxide stream, containing 7.5 ppm hydrogen peroxide, passed through a short preheat line and then upflow through the reactor tube at 185 psig (1274 kPa) and 300° F. (149° C.). Estimated residence time of the liquid in the reactor was about 5 minutes. The reactor effluent passed through a heat exchanger, a back-pressure regulator, and then to a sampling vessel where liquid samples were collected periodically. The liquid samples were analyzed for dissolved metals by ICP after filtration.

Results of Example 4, given in Table III, show the effectiveness of the hydrogen peroxide treatment for removal of iron (Fe) from the purification mother liquor, even in the presence of terephthalic acid and larger amounts of Co and Mn.

TABLE III

| | Purification mother liquor (starting material) | Example 4 |
|---|---|---|
| $H_2O_2$ Employed? | — | Yes |
| Dissolved Fe | 0.56 ppm | 0.12 ppm* |
| Fe Removal | — | 79% |
| Dissolved Mn | 34 ppm | 32.5 ppm* |
| Mn Removal | — | 4% |

TABLE III-continued

| | Purification mother liquor (starting material) | Example 4 |
|---|---|---|
| Dissolved Co | 11.9 ppm | 11.3 ppm* |
| Co Removal | — | 5% |

*Average of 4 samples collected over 2 to 8 hours on stream.

Example 5

In this example, peroxide was added during normal operation of a commercial scale process for oxidation of an aromatic feed material comprising para-xylene to crude terephthalic acid and purification of the resulting crude acid. Oxidation was conducted in a liquid phase reaction mixture in a solvent comprising acetic acid and water and in the presence of a catalyst comprising cobalt and manganese with a source of bromine as promoter and using air as a source of oxygen, with passage of oxidation reactor off-gas comprising vaporized water and acetic acid to a distillation column supplied with liquid reflux and internal titanium packing. Chemical grade hydrogen peroxide, purchased as a 50 wt % solution in water, was pumped via a transfer line, in which it was mixed in-line with a demineralized water stream to dilute the peroxide to approximately 0.3 wt %, into a slurry of solid, purified terephthalic acid that had been introduced into a filter for separation of the solid acid from the liquid. Dissolved iron content of the liquid was about 0.7 to 0.8 ppm by weight. The hydrogen peroxide solution was injected at a rate corresponding to about 10 to 20 g hydrogen peroxide per 1000 kg of purification slurry introduced into the filter. The test was conducted in two intervals, each lasting about 1½ to 2½ consecutive hours. Purified terephthalic acid produced during the trials tested high for color forming impurities but was substantially free of iron otherwise comparable to product produced without peroxide addition. The following table reports iron remaining in the liquid after peroxide treatment.

| Sample | Peroxide Addition (L/hr) | Peroxide in Liquid (ppmw) | Fe in Liquid (wt % of initial Fe) | Fe removed from Liquid (wt %) |
|---|---|---|---|---|
| A | 0.81 | 9 | 37 | 63 |
| B | 0.51 | 5 | 98 | 2 |
| C | 0.82 | 8 | 70 | 30 |
| D | 1.28 | 13 | 43 | 57 |
| E | 1.78 | 18 | 49 | 51 |

As seen from this example and the preceding table, iron was oxidized as a result of hydrogen peroxide addition because levels of dissolved iron in purification mother liquor samples taken after peroxide addition were lower than in samples taken prior to peroxide addition. Concentrations of oxidation catalyst metals present in the mother liquor were not affected by the peroxide addition.

Example 6

Another peroxide addition trial was conducted in a commercial scale purified terephthalic acid manufacturing process involving liquid phase oxidation of para-xylene feed material to crude terephthalic acid and purification of the resulting crude acid. The oxidation was conducted using acetic acid and water as solvent, air as the oxygen source and catalyst comprising cobalt and manganese with bromine as promoter. Reactor off-gas was passed to a distillation column. Reflux to the distillation column included purification mother liquor obtained after separation solid, purified terephthalic acid from the purification solution.

The peroxide used in this example was a semiconductor grade hydrogen peroxide obtained as a 31 wt % solution in water. Peroxide was held in a feed tank and pumped to the outlet of a purification mother liquor hold tank located downstream of filtration of solid purified acid from the purification liquid through a 25.4 cm inner diameter line using a Pulsafeeder diaphragm metering pump with a maximum rate of about 6 liters/hour. The pump had a double diaphragm configuration with diaphragms constructed of a Teflon material for compatibility with peroxide. The hose connecting the peroxide feed tank to the pump was a Teflon-lined hose from Goodyear ("HI-PER", 2.54 cm inner diameter) rated for continuous hydrogen peroxide service. A sample point was located a distance downstream from the injection point pump to correspond to a residence time of about 10 seconds at typical mother liquor flow rates. Although this sampling point provided a somewhat short residence time at typical flow rates, it was considered suitable for purposes of these trials.

The peroxide solution was injected at a rate corresponding to 15 to 17 g hydrogen peroxide solution per 1000 kg mother liquor over a period of about 26 hours in one set of trials and a rate corresponding to 9 to 10 g hydrogen peroxide per 1000 kg mother liquor over a period of about six hours during another trial. In all trials, temperature of the liquid into which the peroxide solution was injected was about 150° C. Samples of the liquid to which the solution had been added were collected at the sample point and analyzed for metals by ICP. Control samples were collected during periods of about one hour while the peroxide injection system was turned off.

Samples taken during the first set of trials showed about 80% lower levels of dissolved iron as a result of injection of the peroxide solution as compared to samples taken when the injection system was not on. Samples taken during the trials with the lower rate of peroxide solution addition resulted in about 40% iron oxidation. Purified terephthalic acid produced during the trials was comparable to commercial product produced during operation without addition of peroxide.

As many different embodiments of this invention may be made without departing from the spirit and scope thereof, it is to be understood that the invention is not limited to the specific embodiments thereof, except as defined in the appended claims and equivalents thereof.

We claim:

1. A process for making an aromatic carboxylic acid wherein amounts of dissolved iron present in liquid streams are controlled comprising steps comprising:
   A) Contacting an oxidizable aromatic feed material with molecular oxygen in the presence of an oxidation catalyst having one or more oxidation catalyst metals with an atomic number of about 21 to about 82 and solvent comprising a $C_2$ to $C_5$ aliphatic carboxylic acid in a liquid phase reaction mixture in a reactor under oxidation conditions to form a solid a crude aromatic carboxylic acid, a liquid comprising solvent and water, and an off-gas comprising vaporized water and vaporized solvent;
   B) Separating solid crude aromatic carboxylic acid from the liquid;
   C) Distilling at least a portion of the off-gas in a distillation column supplied with reflux liquid to separate vaporized solvent from vaporized water such that a liquid stream comprising solvent and a distillation overhead gas comprising vaporized water are formed;
   D) Returning at least a portion of the liquid stream from step C to the reactor;
   E) Dissolving at least a portion of the separated solid crude aromatic carboxylic acid in a purification solvent comprising water to form a liquid purification solution;
   F) Contacting the purification solution with hydrogen in the presence of a Group VIII metal hydrogenation catalyst and under hydrogenation conditions, including temperature of about 450 to about 600° F. and pressure of about 900 to about 1500 psig, effective to form a solution comprising purified aromatic carboxylic acid and liquid comprising purification solvent;
   G) Separating purified aromatic carboxylic acid from the solution comprising purification solvent which results from step F to form a solid, purified aromatic carboxylic acid and a purification mother liquor;
   H) Recycling at least a portion of the purification mother liquor to at least one of step C and step E; and
   I) Adding at least one peroxide of the formula $R_1$—O—O—$R_2$, wherein $R_1$ and $R_2$ are the same or different and are hydrogen or a hydrocarbyl group, to at least one liquid stream resulting from step A or present in or resulting from at least one other step, wherein the peroxide is added in an amount effective to precipitate dissolved iron from the liquid stream.

2. The process of claim 1 wherein peroxide is added to a liquid stream resulting from step A.

3. The process of claim 1 wherein peroxide is added to a liquid stream present in or resulting from step B.

4. The process of claim 1 wherein peroxide is added to a liquid stream present in or resulting from step G.

5. The process of claim 1 wherein peroxide is added to a liquid steam present in or resulting from step H.

6. The process of claim 1 further comprising an oxidation mother liquor recycle step comprising recycling to the liquid phase in the reactor at least a portion of the liquid after separation of the solid crude aromatic carboxylic acid.

7. The process of claim 6 wherein peroxide is added to a liquid stream present in or resulting from the oxidation mother liquor recycle step.

8. The process of claim 1 wherein peroxide is added to at least a portion of the purification mother liquor remaining after separation of the purified aromatic acid in step G, and the purification mother liquor after addition of peroxide is recycled to step C such that the reflux liquid in step C comprises purification solvent.

9. The process of claim 8 wherein the oxidizable feed material is para-xylene.

10. The process of claim 9 wherein the peroxide is hydrogen peroxide.

11. The process of claim 1 wherein the oxidizable aromatic feed material is para-xylene.

12. The process of claim 1 wherein the peroxide is hydrogen peroxide.

13. The process of claim 1 further comprising a step comprising subjecting a liquid stream to which peroxide has been added to a solid-liquid separation suitable for removing solid iron from the liquid stream.

14. A process for controlling amounts of dissolved iron in liquid streams during the manufacture of an aromatic carboxylic acid comprising a step comprising contacting an oxidizable aromatic feed material with molecular oxygen in the presence of an oxidation catalyst having one or more oxidation catalyst metals with an atomic number of about 21 to about 82 and solvent comprising a $C_2$ to $C_5$ aliphatic carboxylic acid in a reactor under oxidation conditions to form a solid crude aromatic acid product, a liquid process stream, and an off-gas comprising vaporized water and vaporized solvent; wherein at least one peroxide of the formula $R_1$—O—O—$R_2$, wherein $R_1$ and $R_2$ are the same or different and are hydrogen or a hydrocarbyl group, is added to at least a portion of the liquid process stream in an amount effective to precipitate dissolved iron from the liquid stream to control amounts of iron dissolved therein.

15. The process of claim 14 wherein the liquid process stream comprises dissolved amounts of at least one oxidation catalyst metal having an atomic number of about 21 to about 82 and wherein the peroxide is added in an amount such that amounts of dissolved iron in the liquid stream are controlled without precipitation of catalyst metal that prevents recycle of the liquid stream.

16. The process of claim 14 further comprising a step comprising separating the liquid process stream from the crude aromatic acid product wherein the peroxide is added to at least a portion of the liquid process stream after separation.

17. The process of claim 16 further comprising a step comprising recycling at least a portion of the liquid process stream to the reactor.

18. The process of claim 14 further comprising a step comprising separating at least a portion of the crude aromatic acid product from at least a portion of the liquid process stream.

19. The process of claim 18 further comprising a step comprising recycling at least a portion of the liquid process stream to the reactor.

20. The process of claim 14 further comprising a step comprising distilling at least a portion of the off-gas to separate vaporized solvent from vaporized water in a distillation column supplied with reflux comprising at least a portion of the liquid process stream, wherein the peroxide is added to the liquid process stream before the reflux is supplied to the distillation column.

21. The process of claim 20 wherein the peroxide is hydrogen peroxide, di-t-butyl peroxide, di-benzoyl peroxide, t-butyl hydro peroxide, or a mixture thereof.

22. The process of claim 14 wherein the oxidation catalyst comprises at least one of cobalt and manganese.

23. The process of claim 14 wherein the oxidizable aromatic feed material is an aromatic compound chosen from ortho-xylene, meta-xylene, para-xylene, 1,5 dimethylnaphthalene, 2,6 dimethylnaphthalene, and mixtures thereof.

24. A process for controlling amounts of dissolved iron in liquid streams during the purification of a crude aromatic carboxylic acid comprising hydrogenating a crude aromatic carboxylic acid in the presence of a Group VIII metal hydrogenation catalyst and solvent comprising water under hydrogenation conditions including temperature of about 450 to about 600° F. and pressure of about 900 to about 1500 psig to form purified aromatic carboxylic acid dissolved in a liquid process stream and adding at least one peroxide of the formula $R_1$—O—O—$R_2$, wherein $R_1$ and $R_2$ are the same or different and are hydrogen or a hydrocarbyl group, to the liquid process stream in an amount effective to precipitate dissolved iron from the liquid stream to control amounts of dissolved iron therein.

25. The process of claim 24 comprising a step wherein at least a portion of the purified aromatic carboxylic acid is precipitated before addition of the peroxide.

26. The process of claim 25 comprising a step wherein at least a portion of the precipitated purified aromatic carboxylic acid is separated from the liquid process stream.

27. The process of claim 24 wherein the peroxide is chosen from hydrogen peroxide, di-t-butyl peroxide, di-benzoyl peroxide, t-butyl hydro peroxide, and mixtures thereof.

28. The process of claim 24 wherein the aromatic carboxylic acid is terephthalic acid.

29. The process of claim 12 wherein 500 ppmw or less sulfate impurities are present in the hydrogen peroxide.

30. The process of claim 12 wherein the hydrogen peroxide is used as solution in water.

* * * * *